United States Patent
Masuda et al.

(10) Patent No.: US 8,663,223 B2
(45) Date of Patent: Mar. 4, 2014

(54) SURGICAL TREATMENT APPARATUS

(75) Inventors: Shinya Masuda, Hino (JP); Hideo Sanai, Hachioji (JP); Takeshi Onaga, Hachioji (JP); Norikiyo Shibata, Sagamihara (JP)

(73) Assignee: Olympus Corporation (JP)

( * ) Notice: Subject to any disclaimer, the term of this patent is extended or adjusted under 35 U.S.C. 154(b) by 167 days.

(21) Appl. No.: 13/281,875

(22) Filed: Oct. 26, 2011

(65) Prior Publication Data

US 2012/0101493 A1    Apr. 26, 2012

Related U.S. Application Data

(63) Continuation of application No. PCT/JP2010/068874, filed on Oct. 25, 2010.

(51) Int. Cl.
*A61B 18/00*    (2006.01)
(52) U.S. Cl.
USPC ............................................. 606/52; 606/169
(58) Field of Classification Search
USPC .......................... 606/27, 34, 41, 51, 52, 167
See application file for complete search history.

(56) References Cited

U.S. PATENT DOCUMENTS

| | | | | |
|---|---|---|---|---|
| 6,129,735 | A * | 10/2000 | Okada et al. | 606/169 |
| 6,139,561 | A * | 10/2000 | Shibata et al. | 606/169 |
| 6,165,191 | A | 12/2000 | Shibata et al. | |
| 6,273,887 | B1 * | 8/2001 | Yamauchi et al. | 606/48 |
| 6,537,291 | B2 * | 3/2003 | Friedman et al. | 606/169 |
| 2005/0192610 | A1 | 9/2005 | Houser et al. | |
| 2007/0167881 | A1 | 7/2007 | Takahashi | |
| 2007/0198005 | A1 * | 8/2007 | Ichihashi et al. | 606/27 |
| 2007/0233060 | A1 | 10/2007 | Hafner | |
| 2008/0132887 | A1 * | 6/2008 | Masuda et al. | 606/37 |
| 2009/0259221 | A1 * | 10/2009 | Tahara et al. | 606/34 |
| 2009/0259244 | A1 | 10/2009 | Shimizu | |

FOREIGN PATENT DOCUMENTS

| | | |
|---|---|---|
| EP | 1 518 505 | 3/2005 |
| EP | 32 074 959 | 7/2009 |

(Continued)

OTHER PUBLICATIONS

International Search Report mailed Nov. 16, 2010 in corresponding PCT International Application No. PCT/JP2010/068874, with English translation.

(Continued)

*Primary Examiner* — Michael Peffley
*Assistant Examiner* — Daniel Fowler
(74) *Attorney, Agent, or Firm* — Ostrolenk Faber LLP

(57) ABSTRACT

A surgical treatment apparatus includes a receptacle which is configured to abut onto a treatment section so that a predetermined clearance is formed between an electrode section and the treatment section when a grip member is closed relative to the treatment section. The surgical treatment apparatus includes a regulating section which is provided in the grip member so that a closing-direction end located on a closing-direction side of the grip member does not protrude from the receptacle toward the closing direction, the regulating section being made of a material harder than the receptacle, and a handle unit configured to operate the grip member so that the regulating section is closed up to a position where the regulating section contacts the treatment section except when the receptacle contacts the treatment section.

5 Claims, 11 Drawing Sheets

(56) References Cited

FOREIGN PATENT DOCUMENTS

| | | |
|---|---|---|
| EP | 2 105 100 | 9/2009 |
| JP | 2000-185052 | 7/2000 |
| JP | 2006-043348 | 2/2006 |
| JP | 2007-050181 | 3/2007 |
| JP | 2008-011987 | 1/2008 |
| JP | 2008-508966 | 3/2008 |
| JP | 2009-160404 | 7/2009 |
| JP | 2009-240773 | 10/2009 |

OTHER PUBLICATIONS

Written Opinion mailed Nov. 16, 20110 in corresponding PCT International Application No. PCT/JP2010/068874.

Search Report issued by European Patent Office and received by applicant on Jul. 30, 2012 in connection with corresponding EP patent application No. EP 10 84 3933.

English translation of the International Preliminary Report on Patentability for corresponding International Application No. PCT/JP2010/068874 mailed on Aug. 16, 2012.

\* cited by examiner

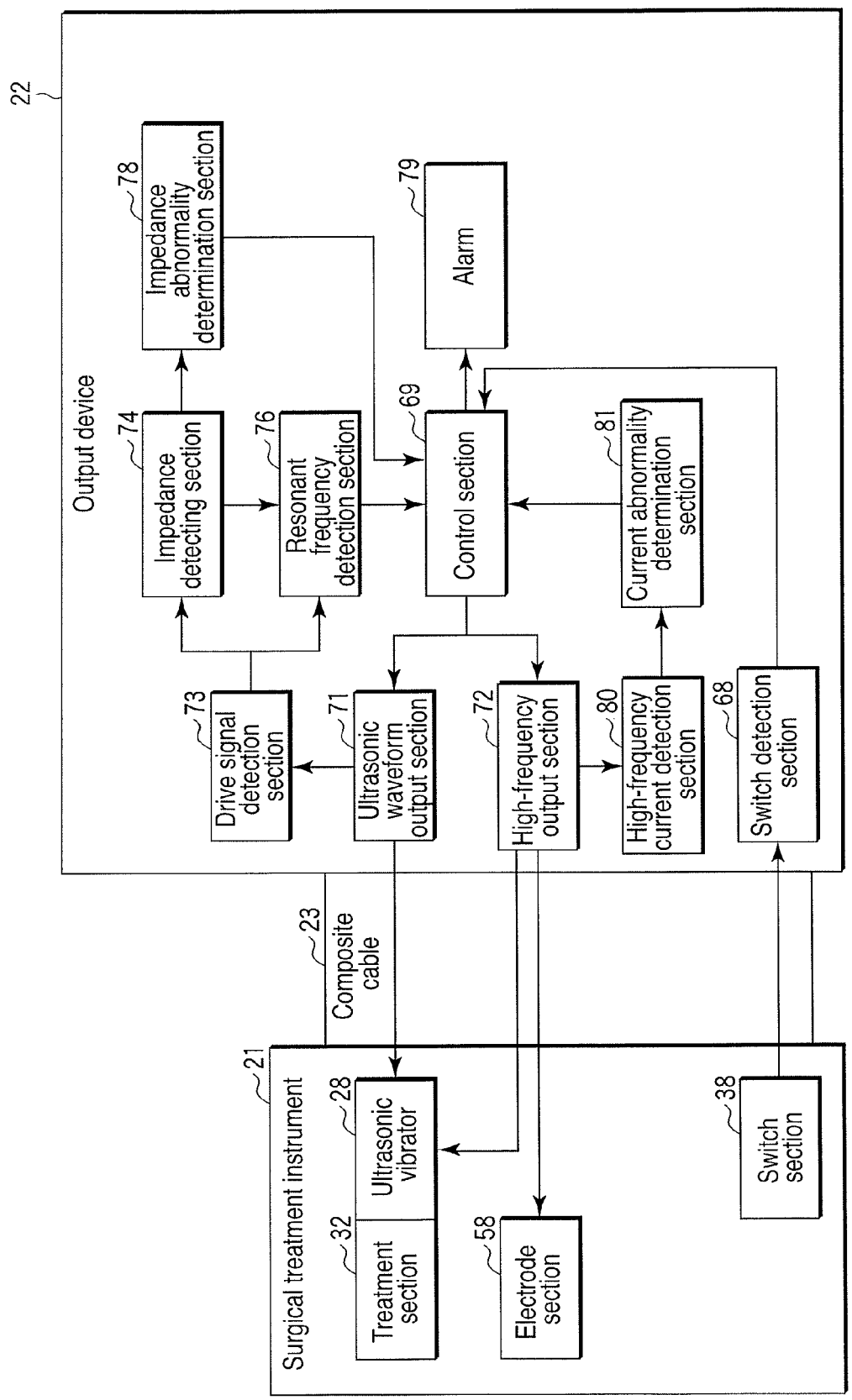
F I G. 8

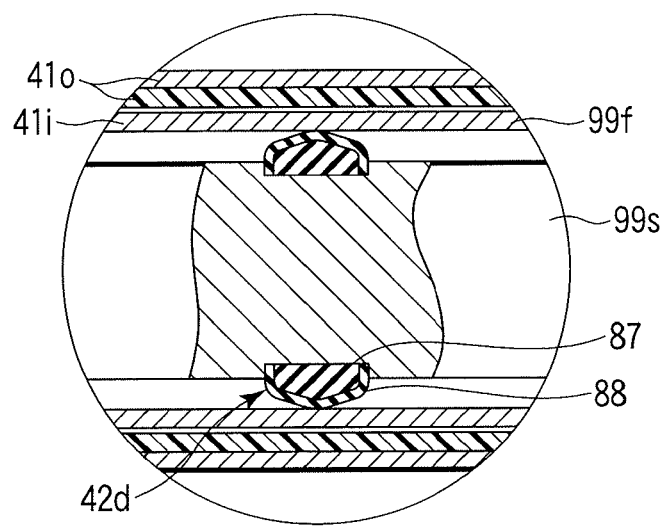
F I G. 15
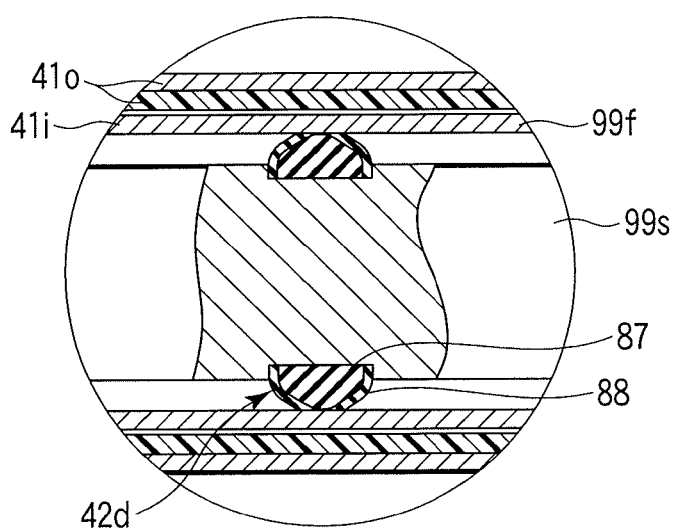
F I G. 16

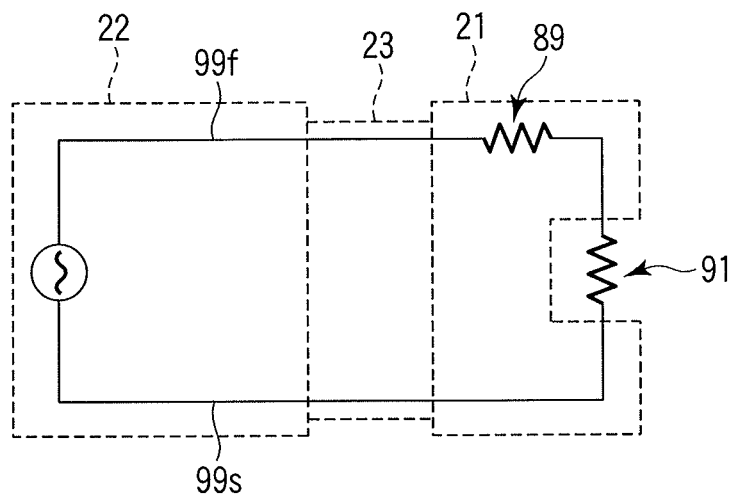
F I G. 19
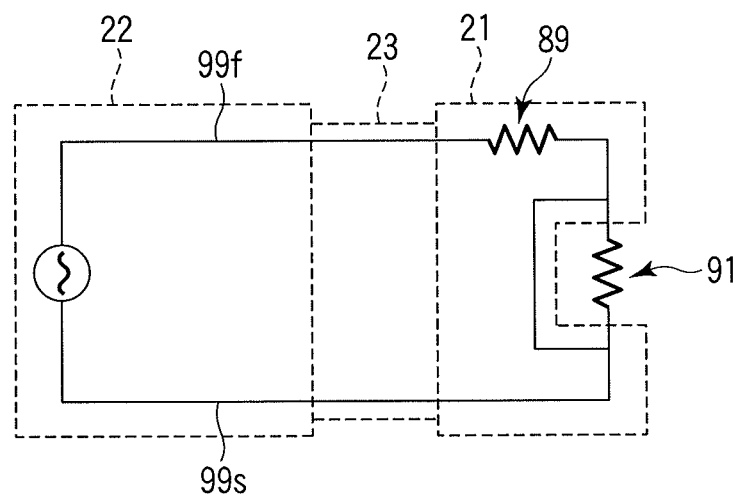
F I G. 20

SURGICAL TREATMENT APPARATUS

CROSS-REFERENCE TO RELATED APPLICATIONS

This is a Continuation Application of PCT Application No. PCT/JP2010/068874, filed Oct. 25, 2010 and based upon and claiming the benefit of priority from prior U.S. Provisional Application No. 61/296,929, filed Jan. 21, 2010, the entire contents of which are incorporated herein by reference.

BACKGROUND OF THE INVENTION

1. Field of the Invention

The present invention relates to a surgical treatment apparatus which uses both ultrasonic vibration and high-frequency current to carry out a surgical treatment on living tissue.

2. Description of the Related Art

Jpn. Pat. Appln. KOKAI Publication No. 2008-11987 has disclosed a surgical treatment instrument which uses both ultrasonic vibration and high-frequency current to treat living tissue. That is, in this surgical treatment instrument, a proximal end portion of a probe is coupled to an ultrasonic vibrator. The probe is inserted through an insertion sheath, and a distal end portion of the probe protrudes from a distal end portion of the insertion sheath to form a treatment section. On the other hand, a grip member that can be opened or closed relative to the treatment section is provided at the distal end portion of the insertion sheath. The grip member is closed relative to the treatment section so that the living tissue can be gripped by the treatment section and the grip member. While the living tissue is gripped by the treatment section and the grip member, ultrasonic vibration generated by the ultrasonic vibrator is transmitted by the probe to ultrasonically vibrate the treatment section. Moreover, a high-frequency voltage is applied between the treatment section and the grip member to pass a high-frequency current through the living tissue. The surgical treatment using ultrasonic vibration provides a satisfactory cutting function, and the surgical treatment using high-frequency current provides a satisfactory coagulation function. The use of these surgical treatments together realizes surgical coagulation/cutting treatments that provide satisfactory cutting and coagulation functions.

BRIEF SUMMARY OF THE INVENTION

According to one aspect of the invention, a surgical treatment apparatus configured to be held and operated by a surgeon, the surgical treatment apparatus includes a vibration generator configured to generate ultrasonic vibration; a vibration transmission section configured to axially transmit the ultrasonic vibration generated in the vibration generator from a proximal end portion to a distal end portion; a treatment section which is formed at the distal end portion of the vibration transmission section, and which is configured to ultrasonically vibrate in an ultrasonic treatment and configured to function as a first electrode in a high-frequency treatment; a grip member which is provided to be openable or closable relative to the treatment section, and which is configured to be closed relative to the treatment section to grip living tissue; an electrode section which is provided in the grip member, and which is configured to function as a second electrode in the high-frequency treatment; a receptacle which is provided in the grip member, and which is configured to abut onto the treatment section so that a predetermined clearance is formed between the electrode section and the treatment section when the grip member is closed relative to the treatment section; a regulating section which is provided in the grip member so that a closing-direction end located on a closing-direction side of the grip member does not protrude from the receptacle toward the closing direction, the regulating section being made of a material harder than the receptacle; and a handle unit configured to operate the grip member so that the regulating section is closed up to a position where the regulating section contacts the treatment section except when the receptacle contacts the treatment section.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 8 is a block diagram showing the surgical treatment system according to the first embodiment of the present invention;

FIG. 15 is a longitudinal sectional view showing a detection rubber lining according to one referential embodiment of a third referential invention in a normal state;

FIG. 16 is a longitudinal sectional view showing the detection rubber lining according to the referential embodiment of the third referential invention in a worn and short-circuited state;

FIG. 19 is a schematic circuit diagram showing the surgical treatment system according to one referential embodiment of a fourth referential invention in a normal state; and FIG. 20 is a schematic circuit diagram showing the surgical treatment system according to the referential embodiment of the fourth referential invention in a short-circuited state.

DETAILED DESCRIPTION OF THE INVENTION

Embodiments of the present invention will be described with reference to the drawings.

The first embodiment of the present invention is described with reference to FIG. 1 to FIG. 7.

Figure 1:
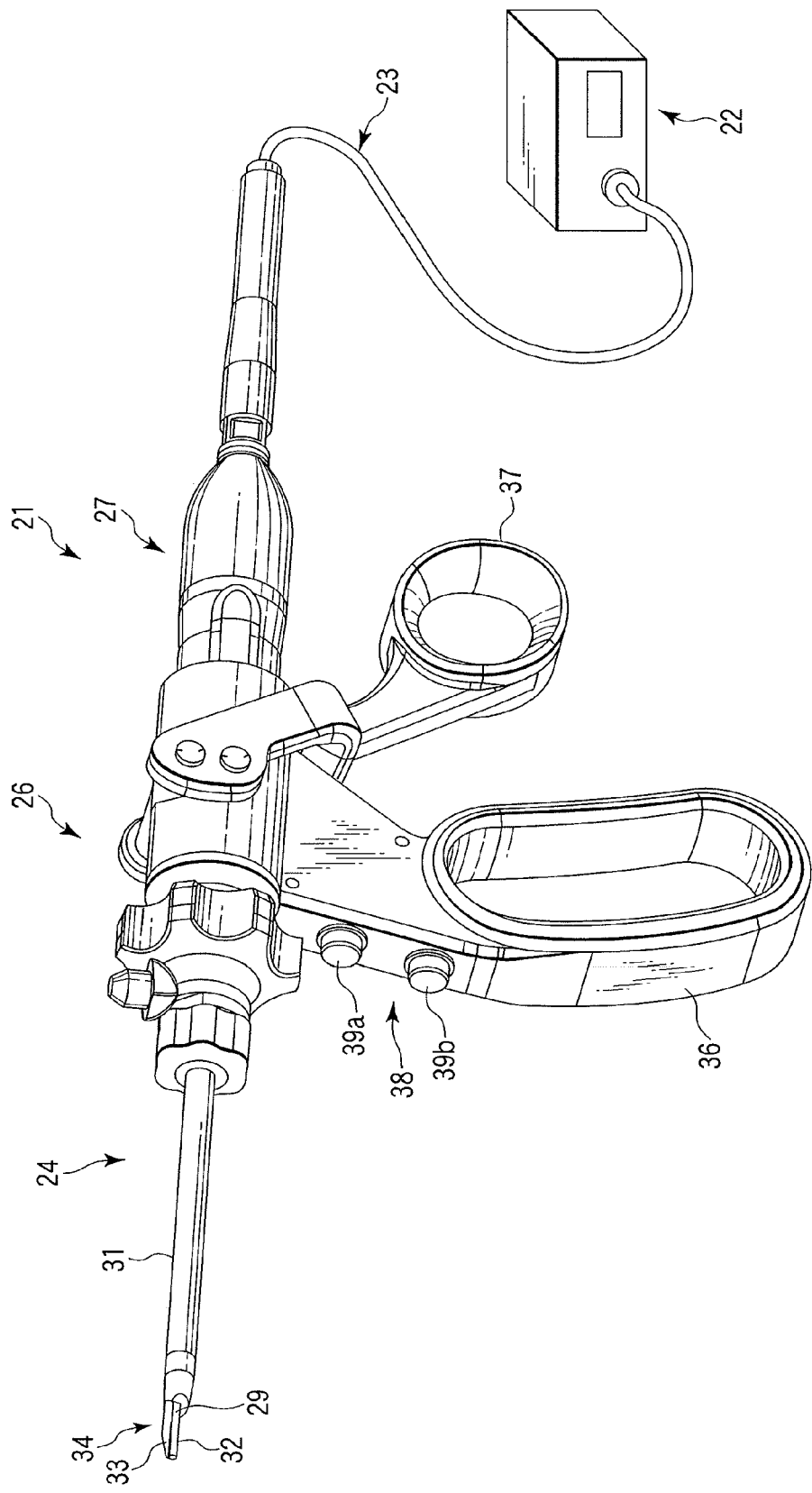
FIG. 1 is a perspective view showing a surgical treatment system according to a first embodiment of the present invention.
Figure 2:
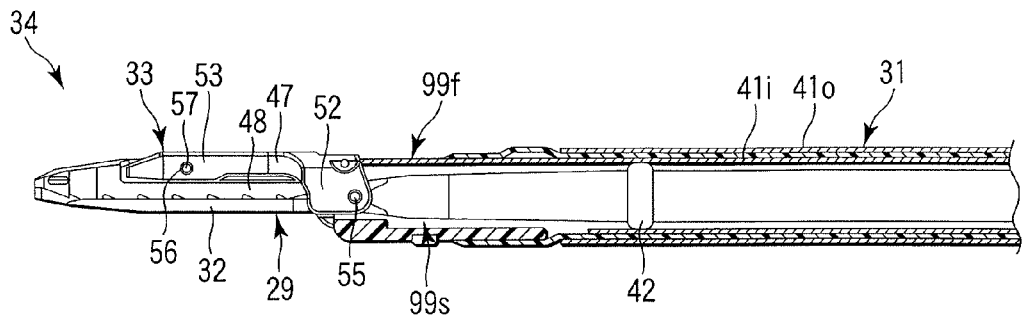
FIG. 2 is a partial longitudinal sectional side view showing a distal grip section according to the first embodiment of the present invention in a closed state.
Figure 3:
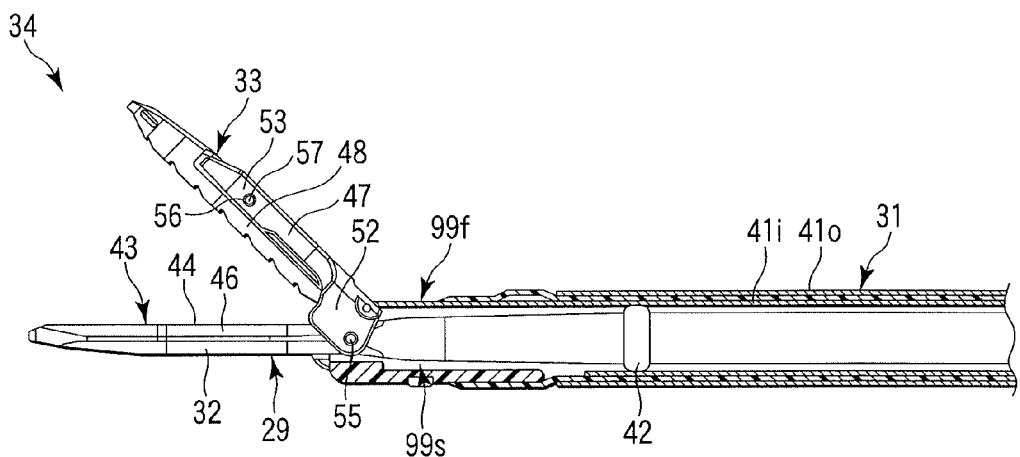
FIG. 3 is a partial longitudinal sectional side view showing the distal grip section according to the first embodiment of the present invention in an open state.
Figure 4:
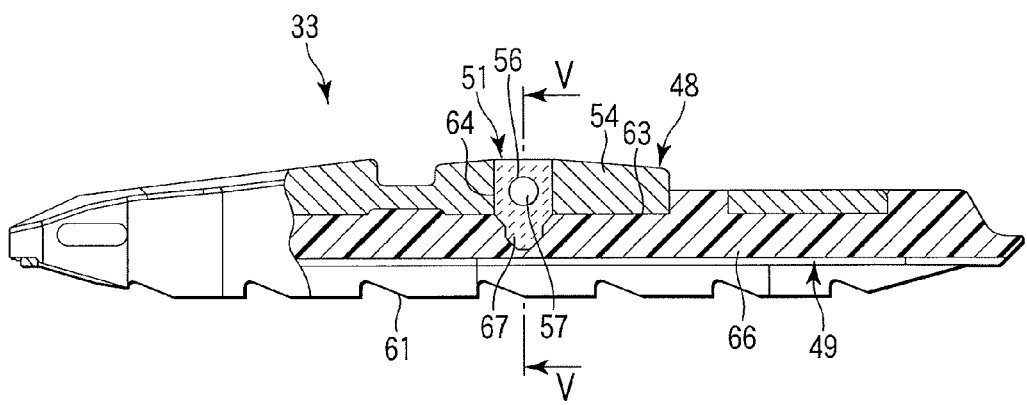
FIG. 4 is a partial longitudinal sectional side view showing a grip member according to the first embodiment of the present invention.
Figure 5:
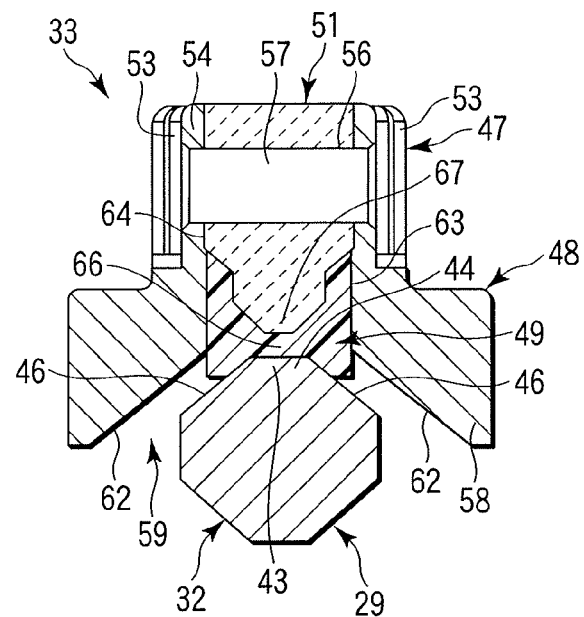
FIG. 5 is a cross-sectional view showing the distal grip section according to the first embodiment of the present invention in a normal state.

A surgical treatment system is described with reference to FIG. 1.

The surgical treatment system according to the first embodiment uses both ultrasonic vibration and high-frequency current to carry out surgical coagulation/cutting treatments on living tissue, and uses high-frequency current to carry out a surgical coagulation treatment on living tissue.

That is, the surgical treatment system includes a surgical treatment instrument 21 as a surgical treatment apparatus configured to be held and operated by a surgeon. The surgical treatment instrument 21 is connected to an output device 22 via a composite cable 23 as a connector.

In the surgical treatment instrument 21, a sheath unit 24, a handle unit 26, and a vibrator unit 27 are detachably connected from the distal side to the proximal side in order. The vibrator unit 27 includes therein an ultrasonic vibrator 28 as a vibration generator. The ultrasonic vibrator 28 is configured to convert a drive signal input from the output device 22 to a mechanical vibration, and configured to generate ultrasonic vibration. A proximal end portion of a probe 29 as a vibration transmission section is coupled to the ultrasonic vibrator 28. The probe 29 is configured to axially transmit the ultrasonic vibration from the proximal end portion to a distal end portion. The probe 29 is inserted through the handle unit 26 and the sheath unit 24. In the sheath unit 24, the probe 29 is inserted through an insertion sheath 31. The distal end portion of the probe 29 protrudes from a distal opening of the insertion sheath 31, thus forming treatment section 32. A grip member 33 is provided at a distal end portion of the insertion sheath 31. The grip member 33 can open or close relative to the treatment section 32 in an opening/closing directions perpendicular to an axial directions of the probe. Thus, a distal grip section 34 is formed by the treatment section 32 and the grip member 33. The handle unit 26 is provided with a fixed handle 36 and a movable handle 37. If the movable handle 37 is turned relative to the fixed handle 36 in the handle unit 26, the grip member 33 is opened or closed relative to the treatment section 32 in the distal grip section 34. The fixed handle 36 is provided with a switch section 38. A cutting switch 39a and a coagulation switch 39b are provided in the switch section 38.

In the surgical treatment system, first and second electrical paths 99f and 99s used in a high-frequency treatment are formed from the output device 22 to the grip member 33 and the treatment section 32 of the surgical treatment instrument 21 via the composite cable 23, respectively.

When the cutting switch 39a of the handle unit 26 is depressed, a drive signal is output to the ultrasonic vibrator 28 from the output device 22. The ultrasonic vibrator 28 to which the drive signal is input generates ultrasonic vibration. The generated ultrasonic vibration is transmitted by the probe 29, and the treatment section 32 at the distal end portion of the probe 29 is ultrasonically vibrated. At the same time, a high-frequency voltage is applied between the grip member 33 and the treatment section 32 via the first and second electrical paths 99f and 99s by the output device 22. On the other hand, when the coagulation switch 39b depressed, no drive signal is output to the ultrasonic vibrator 28 from the output device 22, and a high-frequency voltage is applied between the grip member 33 and the treatment section 32 via the first and second electrical paths 99f and 99s by the output device 22.

The distal grip section 34 of the surgical treatment instrument 21 is described in detail with reference to FIG. 2 to FIG. 7.

Referring to FIG. 2 to FIG. 5, the insertion sheath 31 is formed by an outer sheath 41o and an inner sheath 41i. In the outer sheath 41o, the outside of a conductive metal pipe is covered with an insulating resin tube. The inner sheath 41i is a conductive metal pipe. The inner sheath 41i can be axially moved back and forth relative to the outer sheath 41o.

The probe 29 is made of a conductive material having high acoustic effects and biocompatibility, for example, a titanium alloy such as a Ti-6Al-4V alloy. In the probe 29, an insulating and elastic rubber lining 42 is externally equipped in the position of each node of the ultrasonic vibration. The rubber lining 42 is disposed between the inner sheath 41i and the probe 29 in a compressed state. The probe 29 is held to the inner sheath 41i by the rubber lining 42. A clearance is maintained between the inner sheath 41i and the probe 29.

An abutting portion 43 is formed by the part of the treatment section 32 facing the grip member 33 at the distal end portion of the probe 29. Here, the treatment section 32 is octagonal in its cross section perpendicular to the axial directions of the probe 29. An abutting surface 44 is formed by one surface of the abutting portion 43 facing the grip member 33. A pair of electrode surfaces 46 are formed by surfaces provided to both sides of the abutting surface 44.

The grip member 33 is formed by a body member 47, an electrode member 48, a pad member 49, and a regulating member 51 as a regulating section.

The body member 47 is made of a hard and conductive material. A proximal end portion of the body member 47 constitutes a pivot connection portion 52. The pivot connection portion 52 is pivotally connected to a distal end portion of the outer sheath 41o via a pivot connection shaft 55. The pivot connection shaft 55 extends in width directions perpendicular to both the axial directions and the opening/closing directions. The body member 47 can turn about the pivot connection shaft 55 in the opening/closing directions relative to the outer sheath 41o. A distal end portion of the inner sheath 41i is pivotally connected to the pivot connection portion 52 of the body member 47 at a position provided to the distal side and the opening-direction side of the pivot connection shaft 55. If the movable handle 37 is turned relative to the fixed handle 36 in the handle unit 26, the inner sheath 41i is moved back and forth relative to the outer sheath 41o, and the body member 47 is driven by the inner sheath 41i to turn about the pivot connection shaft 55 in the opening/closing directions relative to the outer sheath 41o. On the other hand, a distal part of the body member 47 constitutes a pair of pivot bearings 53. The pair of pivot bearings 53 are in the form of plates which extend in the axial directions and which are perpendicular to the width directions, and are disposed apart from each other in the width directions.

The electrode member 48 is made of a hard and conductive material. The part of the electrode member 48 provided on the opening-direction side constitutes a pivot support 54. An insertion hole 56 is formed through the pivot support 54 in the width directions. A pivot support shaft 57 is inserted through the insertion hole 56 and extends in the width directions. The pivot support 54 is disposed between the pair of pivot bearings 53 of the body member 47, and is pivotally supported on the pair of pivot bearings 53 via the pivot support shaft 57. The electrode member 48 can oscillate about the pivot support shaft 57 relative to the body member 47. Further, the part of the electrode member 48 provided on the closing-direction side constitutes an electrode section 58. The electrode section 58 extends in the axial directions, and projects to both sides in the width directions. A recessed groove 59 which is open toward the closing direction extends in the axial directions in the part of the electrode section 58 provided on the closing-direction side. Teeth are axially provided in both parts of the groove 59 provided in the closing direction side, thus forming a tooth portion 61. Both side surfaces that define the groove 59 constitute a pair of electrode receiving surfaces 62 that are inclined from the closing direction toward both sides in the width directions. A recessed mating receptacle 63 which is open toward the closing direction axially extends in a bottom portion that defines the groove 59. An embedding hole 64 is formed through the pivot support 54 of the electrode member 48 in the opening/closing directions perpendicularly to the insertion hole 56. The embedding hole 64 is open to the mating receptacle 63.

The pad member 49 is softer than the probe 29, and is made of an insulating material having biocompatibility such as polytetrafluorethylene. The pad member 49 is mated with the mating receptacle 63 of the electrode member 48. The part of the pad member 49 provided on the closing-direction side protrudes from the electrode member 48 to the closing direction, thus forming an abutting receptacle 66. In the cross section perpendicular to the axial directions, the abutting receptacle 66 is in a recessed shape corresponding to the projecting shape of the abutting portion 43 of the treatment section 32. When the grip member 33 is closed relative to the treatment section 32, the abutting portion 43 of the treatment section 32 abuts onto and engages with the abutting receptacle 66 of the pad member 49. The pair of electrode surfaces 46 of the treatment section 32 are arranged parallel to the pair of electrode receiving surfaces 62 of the electrode section 58, and a clearance is maintained between the electrode section 58 and the treatment section 32.

The regulating member 51 is harder than the probe 29, and is made of an insulating high-strength material such as ceramics. The regulating member 51 is pin-shaped. The regulating member 51 is inserted into the embedding hole 64 of the pivot support 54 of the electrode member 48, protrudes toward the mating receptacle 63 of the electrode section 58, and is embedded in the abutting receptacle 66 of the pad member 49 in the mating receptacle 63. A closing-direction end of the regulating member 51 constitutes a regulating end 67. The regulating end 67 does not protrude from the abutting receptacle 66 to the closing direction, and is accommodated in the abutting receptacle 66. The insertion hole 56 is also formed through the regulating member 51, and the pivot support shaft 57 is inserted through the insertion hole 56 of the regulating member 51.

Here, the inner sheath 41i, the body member 47, and the electrode member 48 are electrically connected to one another, and constitute the first electrical path 99f used in a high-frequency surgical treatment. The electrode section 58 of the electrode member 48 functions as one of bipolar electrodes used in a high-frequency surgical treatment. On the other hand, the probe 29 constitutes the second electrical path 99s used in the high-frequency treatment. The treatment section 32 provided to the distal end portion of the probe 29 functions as the other of the bipolar electrodes used in a high-frequency treatment. As described above, the probe 29 is held to the inner sheath 41i by the insulating rubber lining 42, and the clearance is maintained between the inner sheath 41i and the probe 29. This prevents a short circuit between the inner sheath 41i and the probe 29. When the grip member 33 is closed relative to the treatment section 32, the abutting portion 43 of the treatment section 32 abuts onto and engages with the abutting receptacle 66 of the pad member 49. Thus, the pair of electrode surfaces 46 of the treatment section 32 are arranged parallel to the pair of electrode receiving surfaces 62 of the electrode section 58, and the clearance is maintained between the electrode section 58 and the treatment section 32. This prevents a short circuit between the electrode section 58 and the treatment section 32.

Figure 6:
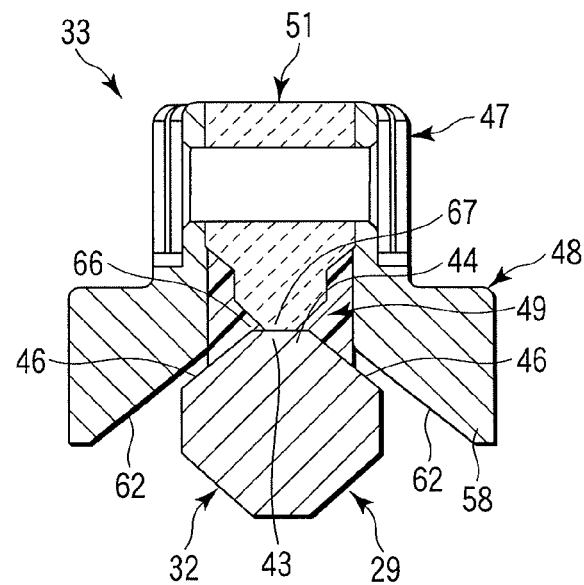
FIG. 6 is a cross-sectional view showing the distal grip section according to the first embodiment of the present invention in a worn state.

Referring to FIG. 6, the pad member 49 is softer than the probe 29. Therefore, the abutting receptacle 66 is worn by the treatment section 32 in the case where the treatment section 32 is ultrasonically vibrated when the grip member 33 is closed relative to the treatment section 32 and the abutting portion 43 of the treatment section 32 abuts onto and engages with the abutting receptacle 66 of the pad member 49. As the abutting receptacle 66 is worn, the clearance between the electrode section 58 and the treatment section 32 is gradually reduced when the abutting portion 43 is in a frictional engagement with the abutting receptacle 66. When the abutting receptacle 66 is worn more than a predetermined amount, the regulating end 67 of the regulating member 51 is exposed from the abutting receptacle 66 in the closing direction. When the regulating end 67 is exposed from the abutting receptacle 66 in the closing direction, the regulating end 67 contacts the treatment section 32 before the electrode section 58 contacts the treatment section 32 if the grip member 33 is closed relative to the treatment section 32. As a result, the contact between the treatment section 32 and the electrode section 58 is regulated. Here, the electrode section 58 and the treatment section 32 are hard. Therefore, when the ultrasonically vibrated treatment section 32 contacts the electrode section 58, the treatment section 32 rapidly and repetitively comes in and out of contact with the electrode section 58. When a high-frequency voltage is applied between the electrode section 58 and the treatment section 32, sparking occurs between the treatment section 32 and the electrode section 58. In the present embodiment, the contact between the treatment section 32 and the electrode section 58 is regulated by the regulating end 67 of the regulating member 51, so that sparking is prevented. The regulating member 51 is made of an insulating material, and is electrically insulated relative to the electrode member 48. Thus, if the ultrasonically vibrated treatment section 32 contacts the regulating end 67 of the regulating member 51, no sparking occurs between the regulating end 67 and the treatment section 32 even when the treatment section 32 rapidly and repetitively comes in and out of contact with the regulating end 67. This prevents sparking between the treatment section 32 and the grip member 33.

Figure 7:
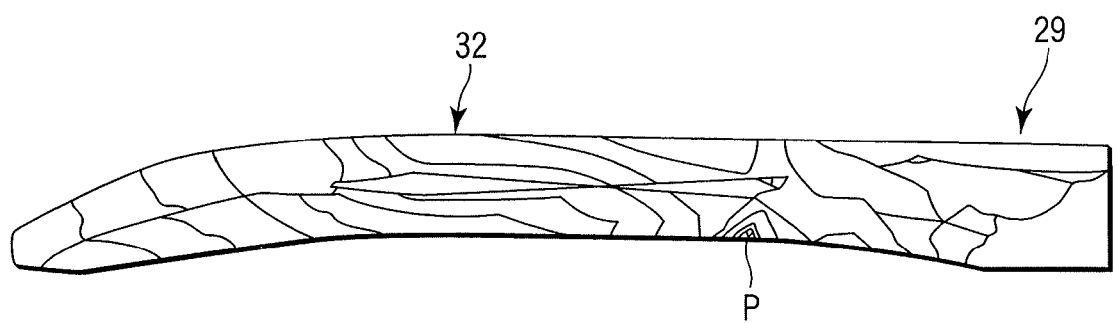
FIG. 7 is a view showing a stress distribution of a treatment section according to the first embodiment of the present invention.

The regulating member 51 is made of a high-strength material harder than the probe 29. Therefore, when the regulating end 67 contacts the ultrasonically vibrated treatment section 32, the regulating member 51 is not worn, and the probe 29 cracks. In the surgical treatment system according to the present embodiment, when the abutting receptacle 66 is worn more than a predetermined amount, the regulating end 67 contacts the treatment section 32 to intentionally crack the probe 29. By detecting this crack, the end of the life of the surgical treatment instrument 21 is detected. Therefore, the position of the contact between the treatment section 32 and the regulating end 67 is set at the stress concentration region in the treatment section 32 to ensure that the probe 29 cracks when the regulating end 67 contacts the treatment section 32. In the linear probe 29, stress concentrates in the positions of the nodes of the ultrasonic vibration, and a stress concentration region is located at the proximal end portion of the treatment section 32. Referring to FIG. 7, a stress concentration region P is located at the curved root of the treatment section 32 in the curved probe 29 that is moderately curved in a J-shape toward the distal end.

The function of the surgical treatment system is described with reference to FIG. 8.

The surgical treatment system, when normally used, carries out coagulation/cutting treatments and a coagulation treatment on living tissue.

That is, when the treatment system is used to carry out coagulation/cutting treatments, living tissue is gripped by the distal grip section 34, and the cutting switch 39a of the handle unit 26 is depressed. The depression of the cutting switch 39a is detected by a switch detection section 68, and a cutting operation signal is output from the switch detection section 68 to a control section 69. The control section 69 to which the cutting operation signal is input is configured to control an ultrasonic waveform output section 71 and a high-frequency output section 72. The ultrasonic waveform output section 71 is configured to output a drive signal to the ultrasonic vibrator 28, and ultrasonic vibration is generated in the ultrasonic vibrator 28. The ultrasonic vibration generated in the ultrasonic vibrator 28 is transmitted by the probe 29, and the treatment section 32 provided at the distal end portion of the probe 29 is ultrasonically vibrated in contact with the gripped living tissue. On the other hand, the high-frequency output section 72 configured to apply a high-frequency voltage between the electrode section 58 and the treatment section 32 via the first and second electrical paths 99f and 99s, and a high-frequency current is passed through the gripped living tissue. Thus, both ultrasonic vibration and high-frequency current are used to carry out, on the living tissue gripped by the distal grip section 34, coagulation/cutting treatments that provide satisfactory cutting and coagulation functions. In order to carry out a coagulation treatment, the coagulation switch 39b of the handle unit 26 is depressed. In this case, a coagulation operation signal is output from the switch detection section 68 to the control section 69. The high-frequency output section 72 is controlled by the control section 69 so that a high-frequency current is passed through the living tissue gripped by the distal grip section 34. In this way, the high-frequency current is used to carry out, on the living tissue gripped by the distal grip section 34, a coagulation treatment that provides a satisfactory coagulation function.

Phase-locked loop control (hereinafter referred to as PLL control) is used by the control section 69 as a method of controlling the ultrasonic waveform output section 71.

That is, the control section 69 is configured to scan the frequency of the drive signal output from the ultrasonic waveform output section 71 within a predetermined range around a previously detected resonant frequency. An output current and an output voltage of the drive signal are detected by a drive signal detection section 73. The drive signal detection section 73 is configured to output the detected output current and output voltage to an impedance detection section 74 and a resonant frequency detection section 76. The impedance detection section 74 is configured to detect impedance from the input output current and output voltage, and configured to output the current and voltage to the resonant frequency detection section 76. The resonant frequency detection section 76 is configured to detect a frequency from the input output current and output voltage, and further configured to detect, as a resonant frequency, a frequency at which the input impedance is minimized, and then output the resonant frequency to the control section 69. The control section 69 is configured to scan the frequency of the drive signal within a predetermined range around the newly input resonant frequency. Thus, the ultrasonic vibrator 28 is always driven at the resonant frequency, so that driving efficiency is improved.

The surgical treatment system, when normally used, is always configured to perform a crack detection to detect cracks caused in the probe 29.

That is, during the normal use of the surgical treatment system, the probe 29 may crack, for example, if the probe 29 is excessively loaded when ultrasonic waveforms are output. In the meantime, the impedance detected by the above-mentioned PLL control is also output to an impedance abnormality determination section 78 from the impedance detection section 74. The impedance abnormality determination section 78 is configured to determine that the probe 29 has cracked if a variation of the impedance per unit time has exceeded an experimentally predetermined threshold. In this way, a crack detection section used in detecting cracks in the probe 29 is formed by the drive signal detection section 73, the impedance detection section 74, the resonant frequency detection section 76, and the impedance abnormality determination section 78. When cracks are detected, the control section 69 is configured to activate an alarm 79 to report the crack to the surgeon, and configured to forcibly stop the output of the drive signal by the ultrasonic waveform output section 71 and also forcibly stop the output of the high-frequency current by the high-frequency output section 72.

The surgical treatment system, when normally used, is always configured to perform short-circuit detection to detect a short circuit between the treatment section 32 and the electrode section 58.

That is, during the normal use of the surgical treatment system, a short circuit may be caused between the treatment section 32 and the electrode section 58 if the treatment section 32 and the electrode section 58 contact the same conductive member when ultrasonic waveforms are output. In the meantime, a high-frequency current detection section 80 is configured to detect the output current of the high-frequency current output from the high-frequency output section 72, and configured to output this current to a current abnormality determination section 81. When the input output current has exceeded a predetermined threshold, the current abnormality determination section 81 is configured to determine that a short circuit has occurred between the treatment section 32 and the electrode section 58. In this way, a short-circuit detection section configured to detect whether a short circuit has occurred between the treatment section 32 and the electrode section 58 is formed by the high-frequency current detection section 80 and the current abnormality determination section 81. When a short circuit is detected, the control section 69 is configured to activate the alarm 79 to report the short circuit to the surgeon, and configured to forcibly stop the output of the high-frequency current by the high-frequency output section 72, and also forcibly stop, if any, the output of the drive signal by the ultrasonic waveform output section 71.

Not only sound but also light or a vibration, for example, may be used to report the crack or short circuit to the surgeon. When the surgical treatment system is used together with an endoscope system, a warning that reports the crack or short circuit may be displayed on a monitor that shows an endoscopic observation image.

Furthermore, the surgical treatment system is configured to perform a life detection to detect the end of the life of the surgical treatment instrument 21.

In the present embodiment, when the abutting receptacle 66 of the pad member 49 is worn more than a predetermined amount, the regulating end 67 of the regulating member 51 contacts the treatment section 32 to intentionally crack the probe 29, and this crack is detected to detect the end of the life of the surgical treatment instrument 21.

That is, when living tissue is gripped by the distal grip section 34 and thus coagulation/cutting treatments are carried out on it, the treatment section 32 is ultrasonically vibrated while the abutting portion 43 of the treatment section 32 abuts onto and engages with the abutting receptacle 66 of the pad member 49. Therefore, after the completion of the cutting, the abutting receptacle 66 is worn by the treatment section 32. As the surgical treatment instrument 21 is repeatedly used, the abutting receptacle 66 is gradually worn, and the surgical treatment instrument 21 comes to the end of its life. In this case, if the abutting receptacle 66 is further worn by the treatment section 32, the regulating end 67 of the regulating member 51 is exposed from the abutting receptacle 66 of the pad member 49 and contacts the treatment section 32, so that the probe 29 cracks. As described above, the surgical treatment system is configured to perform the crack detection when carrying out coagulation/cutting treatments. Therefore, even when the probe 29 has cracked as a result of contact between the regulating end 67 and the treatment section 32, the alarm 79 is activated to report the crack to the surgeon, and the output of the drive signal by the ultrasonic waveform output section 71 and the output of the high-frequency current by the high-frequency output section 72 are forcibly stopped. The use of the surgical treatment instrument 21 is then stopped, and the surgical treatment instrument 21 is properly disposed of. Otherwise, the sheath unit 24 and the probe 29 alone may be disposed of, and the use of the handle unit 26 and the vibrator unit 27 may be continued.

The surgical treatment system according to the present embodiment has the following advantageous effects.

In the surgical treatment system according to the present embodiment, when the grip member 33 is closed relative to the treatment section 32 provided at the distal end portion of the probe 29 after the abutting receptacle 66 of the pad member 49 is worn more than a predetermined amount, the regulating end 67 of the regulating member 51 contacts the treatment section 32 before the electrode section 58 of the grip member 33 contacts the treatment section 32, thereby regulating the contact of the electrode section 58 with the treatment section 32. This prevents sparking between the treatment section 32 and the electrode section 58. Since the regulating member 51 has insulating properties, no sparking occurs between the treatment section 32 and the regulating end 67 even if the regulating end 67 contacts the treatment section 32. This prevents sparking between the treatment section 32 and the grip member 33.

Otherwise, the abutting receptacle 66 of the pad member 49 is worn more than a predetermined amount, so that the regulating end 67 of the regulating member 51 contacts the treatment section 32. In this case, the probe 29 cracks. The crack is then reported by the alarm 79, and the output of the drive signal by the ultrasonic waveform output section 71 and the output of the high-frequency current by the high-frequency output section 72 are stopped. This permits the end of the life of the surgical treatment instrument 21 to be easily recognized, and prevents output from being continued using the cracked probe 29. Here, the regulating end 67 is designed to contact the stress concentration region of the treatment section 32. This ensures that the probe 29 rapidly and certainly cracks when the regulating end 67 contacts the treatment section 32.

Although the regulating member 51 is made of an insulating material in the embodiment described above, the regulating member 51 may be made of a conductive material when the regulating member 51 is insulated from the electrode member 48, for example, by an additional insulating member. Moreover, the regulating end 67 of the regulating member 51 is embedded in the abutting receptacle 66 of the pad member 49. However, the regulating member 51 may be disposed in the grip member 33 in any manner as long as the regulating member 51 contacts the treatment section 32 before the electrode section 58 contacts the treatment section 32 so that the contact of the electrode section 58 with the treatment section 32 can be regulated, when the grip member 33 is closed relative to the treatment section 32 after the abutting receptacle 66 of the pad member 49 is worn more than a predetermined amount.

Figure 9:
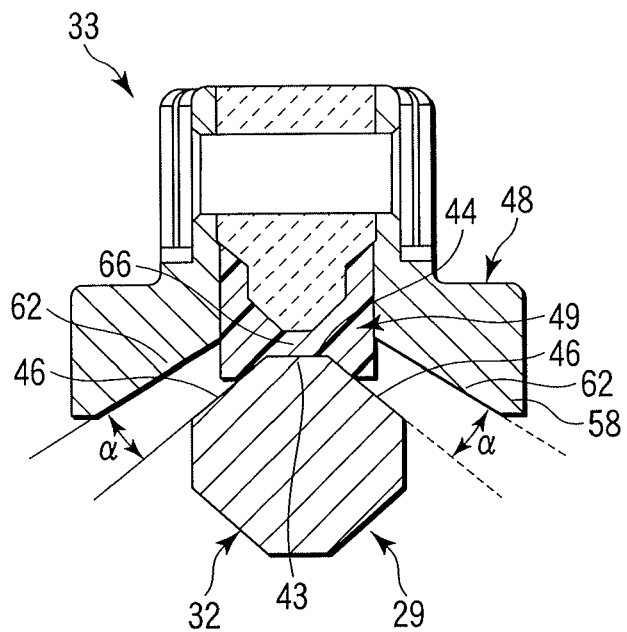
FIG. 9 is a cross-sectional view showing the distal grip section according to a second embodiment of the present invention.

The second embodiment of the present invention is described with reference to FIG. 9.

In the distal grip section 34 according to the present embodiment, a pair of electrode receiving surfaces 62 are formed in the electrode section 58 of the grip member 33, and a pair of electrode surfaces 46 are formed in the abutting portion 43 of the treatment section 32, as in the first embodiment. However, while the abutting portion 43 abuts onto and engages with the abutting receptacle 66 of the pad member 49, the pair of electrode receiving surfaces 62 make a predetermined angle α with the pair of electrode surfaces 46 and form an expanding shape that expands toward the closing direction in a state that the pair of electrode receiving surfaces 62 depart from the pair of electrode surfaces 46 in the width directions. When the grip member 33 is closed relative to the treatment section 32, torsional stress about the axis is applied to the probe 29. This ensures that the contact between the treatment section 32 and the electrode section 58 is prevented even if the probe 29 torsionally deformed.

A first referential invention of the present invention is described below.

Figure 10:
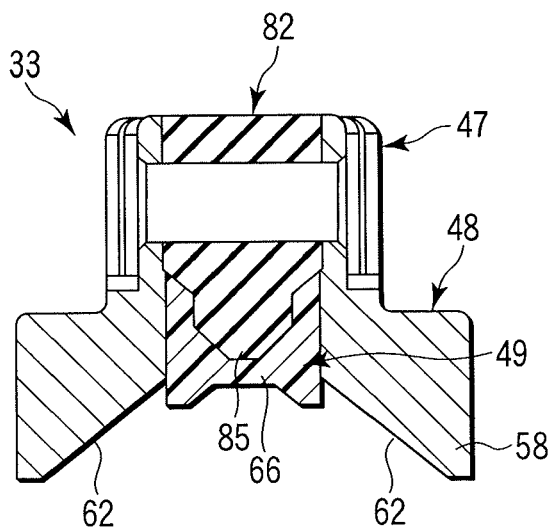
FIG. 10 is a cross-sectional view showing the distal grip section according to one referential embodiment of a first referential invention.

One referential embodiment of the first referential invention is described with reference to FIG. 10.

The surgical treatment system according to the present referential embodiment resembles the surgical treatment system according to the first embodiment in configuration. The difference therebetween is mainly described below.

In the grip member 33 according to the referential embodiment, a deformable member 82 as a deformable section is used instead of the regulating member 51. The deformable member 82 is similar in shape and location to the regulating member 51. However, the deformable member 82 is made of a conductive and elastic material such as conductive rubber, and is electrically connected to the electrode member 48. A closing-direction end of the deformable member 82 constitutes a deformable end 85.

If the abutting receptacle 66 of the pad member 49 is worn more than a predetermined amount and the deformable end 85 of the deformable member 82 is exposed from the abutting receptacle 66, the deformable end 85 contacts the treatment section 32 before the electrode section 58 of the electrode member 48 contacts the treatment section 32 when the grip member 33 is closed relative to the treatment section 32 provided at the distal end portion of the probe 29. Here, the deformable member 82 is made of an elastic material. Therefore, when the treatment section 32 is ultrasonically vibrated, the deformable end 85 is deformed in accordance with the ultrasonic vibration of the treatment section 32 and thus kept in contact with the treatment section 32, and the deformable end 85 does not rapidly come in and out of contact with the treatment section 32. Thus, although the deformable member 82 is made of a conductive material and is electrically connected to the electrode section 58, sparking between the treatment section 32 and the deformable end 85 is avoided, and sparking between the treatment section 32 and the grip member 33 is prevented, even when a high-frequency voltage is applied between the treatment section 32 and the electrode section 58.

Moreover, the surgical treatment system is configured to detect the end of the life of the surgical treatment instrument 21 by detecting a short circuit. That is, the abutting receptacle 66 of the pad member 49 is worn, and the surgical treatment instrument 21 comes to the end of its life. If the abutting receptacle 66 is further worn, the deformable end 85 of the deformable member 82 is exposed from the abutting receptacle 66, and the deformable end 85 contacts the treatment section 32, so that a short circuit occurs between the treatment section 32 and the electrode section 58 via the deformable member 82. The surgical treatment system is configured to perform short-circuit detection when carrying out coagulation/cutting treatments. Thus, even when a short circuit occurs between the electrode section 58 and the treatment section 32 via the deformable member 82 by the contact between the deformable end 85 and the treatment section 32, the alarm 79 is activated to report the short circuit to the surgeon, and the output of the drive signal by the ultrasonic waveform output section 71 and the output of the high-frequency current by the high-frequency output section 72 are forcibly stopped.

The surgical treatment system according to the present embodiment has the following advantageous effects.

In the surgical treatment system according to the present embodiment, when the grip member 33 is closed relative to the treatment section 32 provided at the distal end portion of the probe 29 after the abutting receptacle 66 of the pad member 49 is worn more than a predetermined amount, the deformable end 85 of the deformable member 82 contacts the treatment section 32 before the electrode section 58 of the grip member 33 contacts the treatment section 32. The deformable member 82 is conductive and is electrically connected to the electrode section 58, but is elastic. The deformable end 85 is deformed in accordance with the ultrasonic vibration of the treatment section 32, and kept in contact with the treatment section 32. This avoids sparking between the treatment section 32 and the deformable end 85, and prevents sparking between the treatment section 32 and the grip member 33.

Otherwise, the abutting receptacle 66 of the pad member 49 is worn more than a predetermined amount, so that the deformable end 85 of the deformable member 82 contacts the treatment section 32, and a short circuit occurs between the treatment section 32 and the electrode section 58 via the deformable member 82. In this case, the short circuit is reported, and the output of the drive signal by the ultrasonic waveform output section 71 and the output of the high-frequency current by the high-frequency output section 72 are stopped. This permits the end of the life of the surgical treatment instrument 21 to be easily recognized, and prevents output from being continued while a short circuit is occurring between the treatment section 32 and the electrode section 58.

Figure 11:
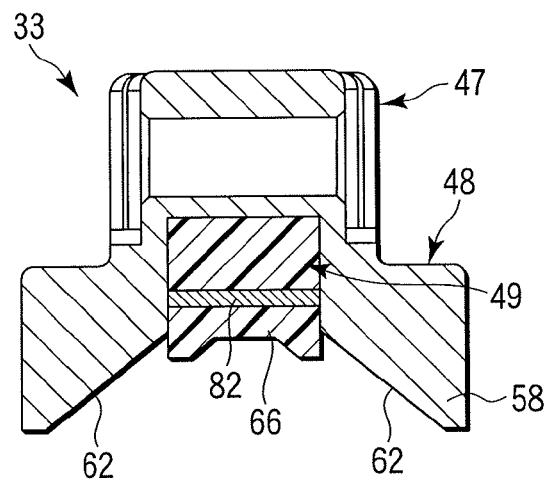
FIG. 11 is a cross-sectional view showing the grip member according to a modification of the referential embodiment of the first referential invention.

A modification of the referential embodiment of the first referential invention is described with reference to FIG. 11.

In the present modification, the deformable member 82 is made of a conductive leaf spring member, or a conductive foil member such as an aluminum foil. In the same manner as the deformable member according to the referential embodiment, the deformable member 82 according to the present modification is deformed in accordance with the ultrasonic vibration of the treatment section 32, and kept in contact with the treatment section 32 to prevent sparking. When the deformable member 82 contacts the treatment section 32, a short circuit occurs between the treatment section 32 and the electrode section 58.

A second referential invention of the present invention is described below.

Figure 12:
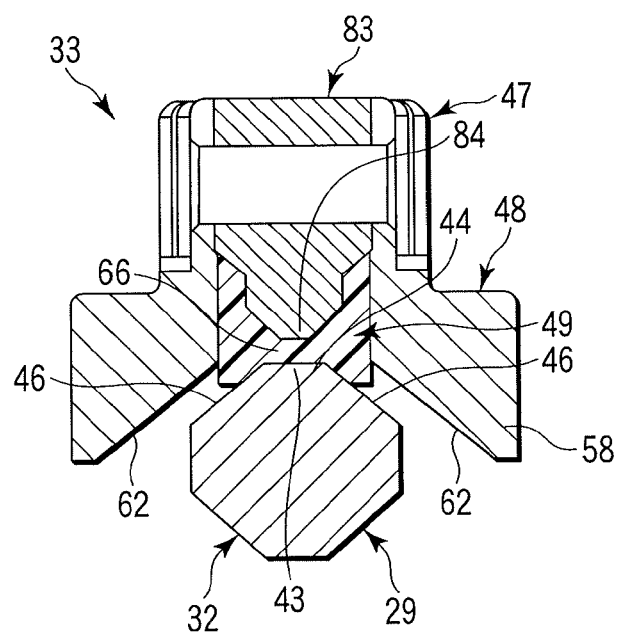
FIG. 12 is a cross-sectional view showing the distal grip section according to one referential embodiment of a second referential invention in a normal state.
Figure 13:
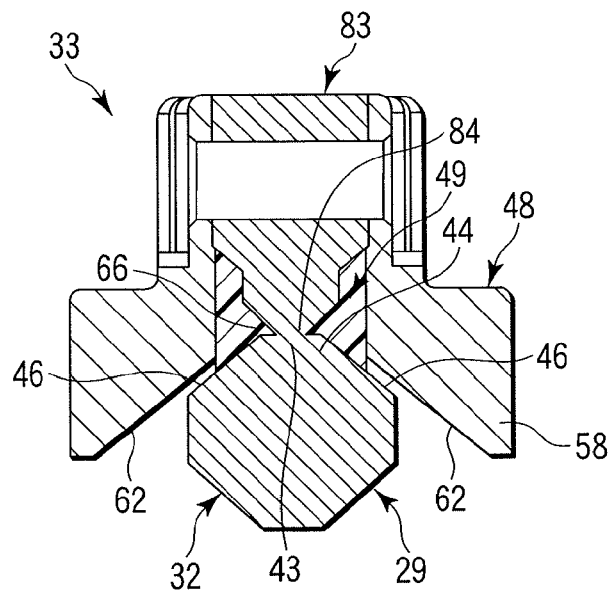
FIG. 13 is a cross-sectional view showing the distal grip section according to the referential embodiment of the second referential invention in a worn and joined state.

One referential embodiment of the second referential invention is described with reference to FIG. 12 and FIG. 13.

The surgical treatment system according to the present referential embodiment resembles the surgical treatment system according to the first embodiment in configuration. The difference therebetween is mainly described below.

In the grip member 33, a fusible member 83 as a fusible section is used instead of the regulating member 51. The fusible member 83 has a pin shape similar to that of the regulating member 51, and is disposed in the same manner as the regulating member 51. However, the fusible member 83 is conductive, and is electrically connected to the electrode member 48 of the grip member 33. A closing-direction end of the fusible member 83 constitutes a fusible end 84. Here, the fusible member 83 is made of a material of the same quality as the probe 29 such that the fusible end 84 and the treatment section 32 are welded together by a short-circuit current when a short circuit occurs between the electrode section 58 and the treatment section 32 provided at the distal end portion of the probe 29 via the fusible member 83. For example, when the probe 29 is made of a Ti-6Al-4V alloy, the fusible member 83 is also made of the Ti-6Al-4V alloy.

If the abutting receptacle 66 of the pad member 49 is worn more than a predetermined amount and the fusible end 84 of the fusible member 83 is exposed from the abutting receptacle 66, the fusible end 84 of the fusible member 83 contacts the treatment section 32 before the electrode section 58 contacts the treatment section 32 when the grip member 33 is closed relative to the treatment section 32 provided at the distal end portion of the probe 29. When a high-frequency voltage is applied between the treatment section 32 and the electrode section 58, a short circuit occurs between the treatment section 32 and the electrode member 48 via the fusible member 83. The fusible member 83 is made of a material of the same quality as the probe 29. The fusible end 84 is welded to the treatment section 32 by a short-circuit current and is kept in contact with the treatment section 32, and does not rapidly and repetitively come in and out of contact with the treatment section 32. This avoids sparking between the treatment section 32 and the fusible end 84, and prevents sparking between the treatment section 32 and the grip member 33.

The fusible end 84 is welded to the treatment section 32, so that the end of the life of the surgical treatment instrument 21 can be recognized, and the surgical treatment instrument 21 cannot be reused. The surgical treatment system is configured to perform short-circuit detection when carrying out coagulation/cutting treatments. Thus, even when a short circuit occurs between the electrode section 58 and the treatment section 32 via the fusible member 83 by the contact between the fusible end 84 and the treatment section 32, the alarm 79 is activated to report the short circuit to the surgeon, and the output of the drive signal by the ultrasonic waveform output section 71 and the output of the high-frequency current by the high-frequency output section 72 are forcibly stopped.

The surgical treatment system according to the present referential embodiment has the following advantageous effects.

In the surgical treatment system according to the present referential embodiment, when the grip member 33 is closed relative to the treatment section 32 provided at the distal end portion of the probe 29 after the abutting receptacle 66 of the pad member 49 is worn more than a predetermined amount, the fusible end 84 of the fusible member 83 contacts the treatment section 32 before the electrode section 58 contacts the treatment section 32. Thus, a short circuit occurs between the treatment section 32 and the electrode section 58 via the fusible member 83, the fusible end 84 is welded to the treatment section 32 by the short-circuit current, and the contact between the treatment section 32 and the fusible end 84 is maintained. This avoids sparking between the treatment section 32 and the fusible end 84, and prevents sparking between the treatment section 32 and the grip member 33. Moreover, the fusible end 84 is welded to the treatment section 32. This permits the end of the life of the surgical treatment instrument 21 to be easily recognized, and ensures that the improper reuse of the surgical treatment instrument 21 is prevented.

Otherwise, the abutting receptacle 66 of the pad member 49 is worn more than a predetermined amount, so that the fusible end 84 of the fusible member 83 contacts the treatment section 32, and a short circuit occurs between the treatment section 32 and the electrode section 58. In this case, the output of the drive signal by the ultrasonic waveform output section 71 and the output of the high-frequency current by the high-frequency output section 72 are stopped. This prevents output from being continued while a short circuit is occurring between the treatment section 32 and the electrode section 58.

Figure 14:
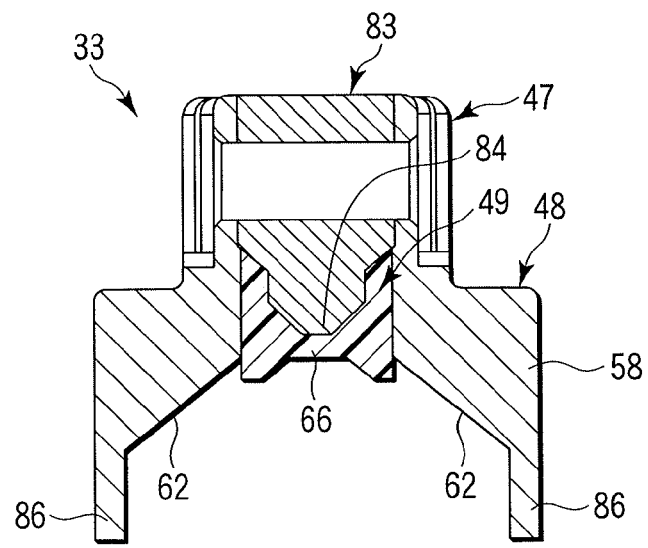
FIG. 14 is a cross-sectional view showing the grip member according to a modification of the referential embodiment of the second referential invention.

A modification of the referential embodiment of the second referential invention is described with reference to FIG. 14.

Here, the distal grip section 34 according to the referential embodiment prevents sparking by welding the fusible end 84 to the treatment section 32. However, sparking may occur between the treatment section 32 and the fusible end 84 only for a short time at the moment when the treatment section 32 and the fusible end 84 contact each other. In the meantime, the grip member 33 according to the present modification uses a pair of walls 86 configured to a spreading of the sparks. That is, the pair of walls 86 extend to the closing direction from both closing-direction ends of the electrode member 48, are disposed substantially perpendicularly to the width directions, and extend in the axial directions. Even if sparking occurs between the treatment section 32 and the fusible end 84, the spreading of the sparks is prevented by the pair of walls 86.

A third referential invention of the present invention is described below.

One referential embodiment of the third referential invention is described with reference to FIG. 15 and FIG. 16.

The surgical treatment system according to the present referential embodiment resembles the surgical treatment system according to the first embodiment in configuration. The difference therebetween is mainly described below.

In the surgical treatment instrument 21 according to the present referential embodiment, the inner sheath 41i as an inner peripheral surface and an inner member is moved back and forth relative to the outer sheath 41o as an outer member in the insertion sheath 31 as a cylindrical member, as with the surgical treatment instrument 21 according to the first embodiment. Thus, the inner sheath 41i opens or closes the grip member 33 relative to the treatment section 32 of the probe 29, and constitutes the first electrical path 99f used in a high-frequency treatment. The probe 29 constitutes the second electrical path 99s used in a high-frequency treatment. The probe 29 is held to the inner sheath 41i by the rubber linings 42.

However, among the rubber linings 42, a most distal side detection rubber lining 42d has its diametrically inner part formed by a conductive section 87 and its diametrically outer part formed by an insulating section 88. The conductive section 87 is made of a conductive and elastic material such as conductive rubber, externally equipped to the probe 29, and electrically connected to the probe 29. On the other hand, the insulating section 88 is made of an insulating and elastic material such as insulating rubber, covered with the diametrically outer surface of the conductive section 87, disposed between the conductive section 87 and the inner sheath 41i, and insulates the conductive section 87 and the inner sheath 41i from each other. The insulating section 88 is worn as a result of mechanical friction between the insulating section 88 and the inner surface of the inner sheath 41i caused by the back-and-forth motion of the inner sheath 41i and as a result of melting attributed to heat caused by the friction. Here, when the abutting receptacle 66 of the pad member 49 is worn in the distal grip section 34 and then the grip member 33 is closed relative to the treatment section 32, the conductive section 87 is exposed by the wear of the insulating section 88, and the conductive section 87 contacts the inner sheath 41i, before the electrode section 58 of the grip member 33 contacts the treatment section 32 provided at the distal end portion of the probe 29.

When living tissue is treated by the surgical treatment system, the movable handle 37 is turned relative to the fixed handle 36 in the handle unit 26, so that the inner sheath 41i is moved back and forth relative to the outer sheath 41o, and the grip member 33 is opened/closed relative to the treatment section 32. As a result of the back-and-forth motion of the inner sheath 41i, the insulating section 88 is worn by the friction between the inner surface of the inner sheath 41i and the insulating section 88. Here, when the abutting receptacle 66 of the pad member 49 is worn and then the grip member 33 is closed relative to the treatment section 32, the conductive section 87 is exposed by the wear of the insulating section 88, and the conductive section 87 contacts the inner sheath 41i, before the electrode section 58 of the grip member 33 contacts the treatment section 32. As a result, when high-frequency waveforms are output, a short circuit occurs between the first electrical path 99f of the inner sheath 41i and the second electrical path 99s of the probe 29 via the conductive section 87. The surgical treatment system is configured to perform short-circuit detection when the high-frequency waveforms are output. Thus, when a short circuit occurs between the first electrical path 99f and the second electrical path 99s via the conductive section 87, the alarm 79 is activated to report the short circuit to the surgeon, and the output of the drive signal by the ultrasonic waveform output section 71 and the output of the high-frequency current by the high-frequency output section 72 are forcibly stopped. In the present referential embodiment, the end of the life of the surgical treatment instrument 21 is detected by the short-circuit detection, and the use of the surgical treatment instrument 21 is ended before the abutting receptacle 66 of the pad member 49 is worn and the electrode section 58 of the grip member 33 contacts the treatment section 32 to cause sparking. This avoids sparking between the treatment section 32 and the electrode section 58, and prevents sparking between the treatment section 32 and the grip member 33.

The surgical treatment system according to the present referential embodiment has the following advantageous effects.

In the surgical treatment system according to the present referential embodiment, before the abutting receptacle 66 of the pad member 49 is worn so that the electrode section 58 of the grip member 33 contacts the treatment section 32 provided at the distal end portion of the probe 29 and sparking occurs between the treatment section 32 and the electrode section 58, the insulating section 88 of the detection rubber lining 42d is worn by the friction between the inner sheath 41i and the insulating section 88. Accordingly, the conductive section 87 of the detection rubber lining 42d contacts the inner sheath 41i, and a short circuit occurs between the first electrical path 99f of the inner sheath 41i and the second electrical path 99s of the probe 29 via the conductive section 87. Thus, the end of the life of the surgical treatment instrument 21 is detected by the short-circuit detection, and the use of the surgical treatment instrument 21 is stopped. This avoids sparking between the treatment section 32 and the electrode section 58, and prevents sparking between the treatment section 32 and the grip member 33. Moreover, the output of the drive signal by the ultrasonic waveform output section 71 and the output of the high-frequency current by the high-frequency output section 72 are stopped by the short-circuit detection. This permits the end of the life of the surgical treatment instrument 21 to be easily recognized, and prevents output from being continued while a short circuit is occurring between the first electrical path 99f and the second electrical path 99s.

Figure 17:
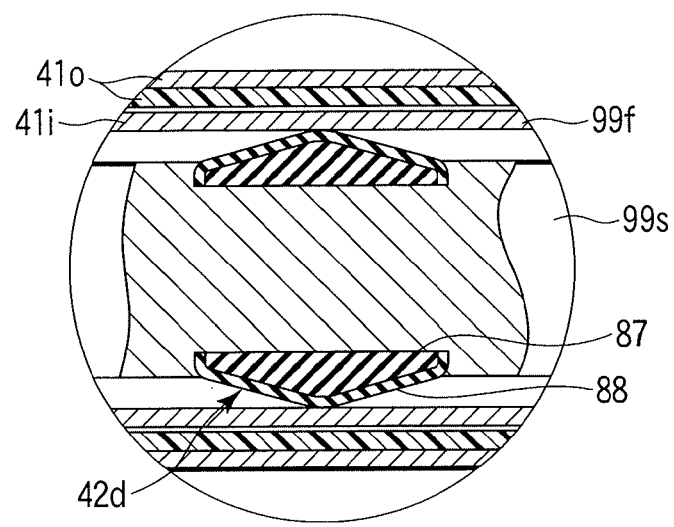
FIG. 17 is a longitudinal sectional view showing the detection rubber lining according to a modification of the referential embodiment of the third referential invention in a normal state.
Figure 18:
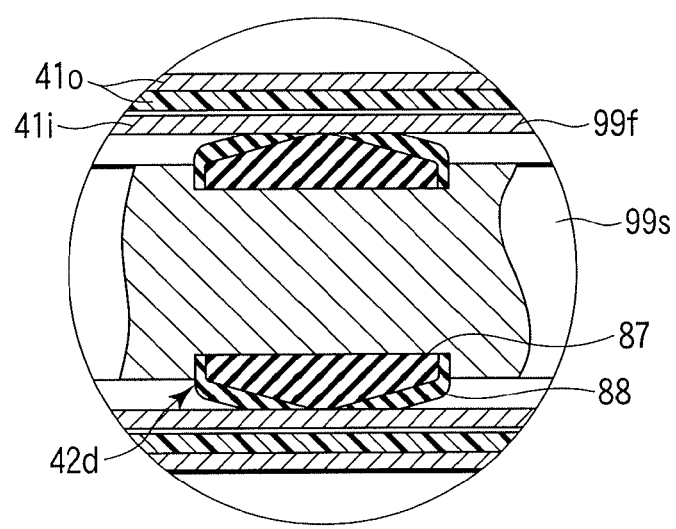
FIG. 18 is a longitudinal sectional view showing the detection rubber lining according to a modification of the referential embodiment of the third referential invention in a worn and short-circuited state.

A modification of the referential embodiment of the third referential invention is described with reference to FIG. 17 and FIG. 18.

In the surgical treatment instrument 21 according to the present referential embodiment, the most distal side detection rubber lining 42d is disposed in a position different from the position of the node of the ultrasonic vibration in the probe 29. Thus, the detection rubber lining 42d is ultrasonically vibrated in the axial directions together with the probe 29, and is worn as a result of mechanical friction between the detection rubber lining 42d and the inner surface of the inner sheath 41i attributed to the ultrasonic vibration and as a result of melting attributed to heat caused by the friction.

A fourth referential invention of the present invention is described below.

One referential embodiment of the fourth referential invention is described with reference to FIG. 19 and FIG. 20.

The surgical treatment system according to the present referential embodiment resembles the surgical treatment system according to the first embodiment in configuration. The difference therebetween is mainly described below.

In the surgical treatment system according to the present referential embodiment, the first electrical path 99f used in a high-frequency treatment is formed from the high-frequency output section 72 of the output device 22 to the electrode section 58 of the grip member 33 of the surgical treatment instrument 21, and the second electrical path 99s used in a high-frequency treatment is formed from the high-frequency output section 72 of the output device 22 to the treatment section 32 of the probe 29 of the surgical treatment instrument 21, as in the surgical treatment system according to the first embodiment. Further, in the surgical treatment instrument 21, a noninductive resistance 89 of 10 to 1000Ω lies in the first electrical path 99f. The noninductive resistance 89 may lie in the second electrical path 99s rather than in the first electrical path 99f. No regulating member 51 is provided in the grip member 33.

As shown in FIG. 19, when a treatment is carried out with the surgical treatment system, living tissue 91 is gripped by the electrode section 58 of the grip member 33 and the treatment section 32 of the probe 29. The first electrical path 99f and the second electrical path 99s are electrically connected to each other by the gripped living tissue 91 so that a closed circuit is formed and a high-frequency current is passed through this closed circuit. In the closed circuit, the living tissue 91 functions as an electrical resistance. Here, as the noninductive resistance is less than or equal to 1000Ω, a necessary degree of high-frequency current is passed through the living tissue 91, and a sufficient coagulation function is ensured.

As shown in FIG. 20, when the electrode section 58 of the grip member 33 is closed relative to the treatment section 32 provided at the distal end portion of the probe 29 after the abutting receptacle 66 of the pad member 49 is worn more than a predetermined amount, the electrode section 58 contacts the treatment section 32, and the treatment section 32 rapidly and repetitively comes in and out of contact with the electrode section 58 simultaneously with the application of a high-frequency voltage between the electrode section 58 and the treatment section 32. However, as the noninductive resistance 89 greater than or equal to 10Ω lies in the first electrical path 99f, the passage of an excessive current through the closed circuit is avoided. This avoids sparking between the treatment section 32 and the electrode section 58, and prevents sparking between the treatment section 32 and the grip member 33.

The resistance value of the noninductive resistance 89 is preferably adjusted in each surgical treatment instrument 21, and the noninductive resistance 89 is preferably provided in the surgical treatment instrument 21 rather than in the output device 22. Even when the noninductive resistance 89 is provided in the surgical treatment instrument 21, heat generation is avoided in the noninductive resistance 89, which prevents the surgeon from feeling discomfort from the heat generation. Moreover, the surgical treatment instrument 21 does not need to be provided with any additional cooling mechanism, which prevents the surgical treatment instrument 21 from increasing in size and decreasing in operability.

Instead of the noninductive resistance 89, it is also possible to use a normal electrical resistance that generates heat. In this case, it is preferable to dispose the electrical resistance in the output device 22, and use an existing cooling mechanism of the output device 22 to cool the electrical resistance.

The technical features of the referential inventions of the present invention are additionally noted below.

According to one referential aspect of the first referential invention of the present invention, a surgical treatment apparatus configured to be held and operated by a surgeon includes a vibration generator configured to generate ultrasonic vibration; a vibration transmission section configured to axially transmit the ultrasonic vibration generated in the vibration generator from a proximal end portion to a distal end portion, the vibration transmission section including a treatment section which is formed at the distal end portion of the vibration transmission section and which is configured to ultrasonically vibrate in an ultrasonic treatment and configured to function as a first electrode in a high-frequency treatment; and a grip member which is openable or closable relative to the treatment section and which is configured to be closed relative to the treatment section to grip living tissue between the grip member and the treatment section, the grip member including a receptacle configured to contact the treatment section and to be worn by the ultrasonic vibration of the treatment section when the grip member is closed relative to the treatment section, an electrode section which is insulated from the receptacle and which is located apart from the treatment section when the treatment section contacts the receptacle and which is configured to function as a second electrode in the high-frequency treatment, and a deformable section which is conductive and which is electrically connected to the electrode section, the deformable section being configured to contact the treatment section before the electrode section when the grip member is closed relative to the treatment section after the receptacle is worn more than a predetermined amount, and the deformable section being configured to be deformed in accordance with the ultrasonic vibration of the treatment section and to be kept in contact with the treatment section when the treatment section is ultrasonically vibrating.

In the surgical treatment apparatus according to the present referential aspect, the deformable section contacts the treatment section before the electrode section contacts the treatment section when the grip member is closed relative to the treatment section after the receptacle is worn more than a predetermined amount. The deformable section is conductive and is electrically connected to the electrode section. However, the deformable section is deformed in accordance with the ultrasonic vibration of the treatment section, and kept in contact with the treatment section. This avoids sparking between the treatment section and the deformable section, and prevents sparking between the treatment section and the grip member.

According to one preferred referential aspect of the present referential invention, a surgical treatment system includes the surgical treatment apparatus; an output device configured to perform an output to the surgical treatment apparatus; and a connector which electrically connects the surgical treatment apparatus and the output device to each other, wherein the output device includes an ultrasonic waveform output section configured to output, to the vibration generator, a drive signal to drive the vibration generator, a high-frequency output section configured to output a high-frequency current used in the high-frequency treatment to the treatment section and the electrode section, a short-circuit detection section configured to detect whether a short circuit has occurred between the treatment section and the electrode section, and a control section configured to control the ultrasonic waveform output section and the high-frequency output section, the control section being configured to stop the output of the drive signal to the vibration generator by the ultrasonic waveform output section and also to stop the output of the high-frequency current to the treatment section and the electrode section by the high-frequency output section when the short-circuit detection section detects a short circuit.

In the surgical treatment system according to the present referential aspect, when the receptacle is worn more than a predetermined amount so that the deformable section contacts the treatment section and a short circuit occurs between the treatment section and the electrode section via the deformable section, the output of the drive signal by the ultrasonic waveform output section and the output of the high-frequency current by the high-frequency output section are stopped. This permits the end of the life of the surgical treatment apparatus to be easily recognized, and prevents output from being continued while a short circuit is occurring between the treatment section and the electrode section.

According to one referential aspect of the second referential invention of the present invention, a surgical treatment apparatus configured to be held and operated by a surgeon includes a vibration generator configured to generate ultrasonic vibration; a vibration transmission section configured to axially transmit the ultrasonic vibration generated in the vibration generator from a proximal end portion to a distal end portion, the vibration transmission section including a treatment section which is formed at the distal end portion of the vibration transmission section and which is configured to ultrasonically vibrate in an ultrasonic treatment and configured to function as a first electrode in a high-frequency treatment; and a grip member which is openable or closable relative to the treatment section and which is configured to be closed relative to the treatment section to grip living tissue between the grip member and the treatment section, the grip member including a receptacle configured to contact the treatment section and to be worn by the ultrasonic vibration of the treatment section when the grip member is closed relative to the treatment section, an electrode section which is insulated from the receptacle and which is located apart from the treatment section when the treatment section contacts the receptacle and which is configured to function as a second electrode in the high-frequency treatment, and a fusible section which is conductive and which is electrically connected to the electrode section, the fusible section being configured to contact the treatment section before the electrode section when the grip member is closed relative to the treatment section after the receptacle is worn more than a predetermined amount, and the fusible section being configured to be welded to the treatment section by a short-circuit current resulting from a short circuit between the treatment section and the electrode section when a high-frequency voltage is applied between the treatment section and the electrode section.

In the surgical treatment apparatus according to the present referential embodiment, the fusible section contacts the treatment section before the electrode section contacts the treatment section when the grip member is closed relative to the treatment section after the receptacle is worn more than a predetermined amount. Thus, a short circuit occurs between the treatment section and the electrode section via the fusible section, the fusible section is welded to the treatment section by the short-circuit current, and contact between the treatment section and the fusible section is maintained. This avoids sparking between the treatment section and the deformable section, and prevents sparking between the treatment section and the grip member. Moreover, the fusible section is welded to the treatment section. This permits the end of the life of the surgical treatment apparatus to be easily recognized, and ensures that the improper reuse of the surgical treatment apparatus is prevented.

According to one preferred referential aspect of the present referential invention, a surgical treatment system includes the surgical treatment apparatus; an output device configured to perform an output to the surgical apparatus; and a connector which electrically connects the surgical treatment apparatus and the output device to each other, wherein the output device includes an ultrasonic waveform output section configured to output, to the vibration generator, a drive signal to drive the vibration generator, a high-frequency output section configured to output a high-frequency current used in the high-frequency treatment to the treatment section and the electrode section, a short-circuit detection section configured to detect whether a short circuit has occurred between the treatment section and the electrode section, and a control section configured to control the ultrasonic waveform output section and the high-frequency output section, the control section being configured to stop the output of the drive signal to the vibration generator by the ultrasonic waveform output section and also to stop the output of the high-frequency current to the treatment section and the electrode section by the high-frequency output section when the short-circuit detection section detects a short circuit.

In the surgical treatment system according to the present referential aspect, when the receptacle is worn more than a predetermined amount so that the fusible section contacts the treatment section and a short circuit occurs between the treatment section and the electrode section, the output of the drive signal by the ultrasonic waveform output section and the output of the high-frequency current by the high-frequency output section are stopped. This prevents output from being continued while a short circuit is occurring between the treatment section and the electrode section.

According to one referential aspect of the third referential invention of the present invention, a surgical treatment system includes a surgical apparatus configured to be held and operated by a surgeon; an output device configured to perform an output to the surgical treatment apparatus; and a connector which electrically connects the surgical treatment apparatus and the output device to each other, wherein the surgical treatment apparatus includes a vibration generator configured to generate ultrasonic vibration, a vibration transmission section configured to axially transmit the ultrasonic vibration generated in the vibration generator from a proximal end portion to a distal end portion and configured to function as a first electrical path in a high-frequency treatment, the vibration transmission section including a treatment section which is formed at the distal end portion of the vibration transmission section and which is configured to ultrasonically vibrate in an ultrasonic treatment and which functions as a first electrode in the high-frequency treatment, a cylindrical member through which the vibration transmission section is inserted, the cylindrical member including an inner peripheral surface configured to function as a second electrical path in the high-frequency treatment, a holding member which is provided in the vibration transmission section and which is elastic, the holding member being compressed between the inner peripheral surface and the vibration transmission section and configured to hold the vibration transmission section to the cylindrical member, and a grip member which is provided at a distal end portion of the cylindrical member and which is openable or closable relative to the treatment section and which is configured to be closed relative to the treatment section to grip living tissue between the grip member and the treatment section, the grip member including a receptacle configured to contact the treatment section and to be worn by the ultrasonic vibration of the treatment section when the grip member is closed relative to the treatment section, and an electrode section which is insulated from the receptacle and which is located apart from the treatment section when the treatment section contacts the receptacle and which is configured to function as a second electrode in the high-frequency treatment, the holding member includes a conductive section which is provided to the vibration transmission section and which is conductive and which electrically connected to the vibration transmission section, and an insulating section which is disposed between the inner peripheral surface and the conductive section and which has insulating properties and which configured to insulate the conductive section from the inner peripheral surface, the insulating section being configured to be worn by friction between the insulating section and the inner peripheral surface so that the conductive section contacts the inner peripheral surface before the receptacle is worn more than a predetermined amount, and the output device includes an ultrasonic waveform output section configured to output, to the vibration generator, a drive signal to drive the vibration generator, a high-frequency output section configured to output a high-frequency current in the high-frequency treatment to the treatment section and the electrode section, a short-circuit detection section configured to detect whether a short circuit has occurred between the first electrical path and the second electrical path, and a control section configured to control the ultrasonic waveform output section and the high-frequency output section, the control section being configured to stop the output of the drive signal to the vibration generator by the ultrasonic waveform output section and also to stop the output of the high-frequency current to the treatment section and the electrode section by the high-frequency output section when the short-circuit detection section detects a short circuit.

In the surgical treatment apparatus according to the present referential aspect, before the receptacle is worn and the electrode section contacts the treatment section so that sparking occurs between the treatment section and the electrode section, the insulating section is worn by the friction between the insulating section and the inner peripheral surface of the cylindrical member. Thus, the conductive section contact the inner peripheral surface, and a short circuit occurs between the vibration transmission section serving as the first electrical path and the inner peripheral surface serving as the second electrical path via the conductive section. Therefore, the end of the life of the surgical treatment apparatus is detected by the detection of the short circuit, and the use of the surgical treatment apparatus is ended. This avoids sparking between the treatment section and the electrode section, and prevents sparking between the treatment section and the grip member. Moreover, the output of the drive signal by the ultrasonic waveform output section and the output of the high-frequency current by the high-frequency output section are stopped by the detection of the short circuit. This permits the end of the life of the surgical treatment apparatus to be easily recognized, and prevents output from being continued while a short circuit is occurring between the first electrical path and the second electrical path.

According to one referential aspect of the fourth referential invention of the present invention, a surgical treatment system includes a surgical treatment apparatus configured to be held and operated by a surgeon; an output device configured to perform an output to the surgical treatment apparatus; and a connector which electrically connects the surgical treatment apparatus and the output device to each other, wherein the surgical treatment apparatus includes a vibration generator configured to generate ultrasonic vibration, a vibration transmission section configured to axially transmit the ultrasonic vibration generated in the vibration generator from a proximal end portion to a distal end portion, the vibration transmission section including a treatment section which is formed at the distal end portion of the vibration transmission section and which is configured to ultrasonically vibrate in an ultrasonic treatment and configured to function as a first electrode in a high-frequency treatment, and a grip member which is openable or closable relative to the treatment section and which is configured to be closed relative to the treatment section to grip living tissue between the grip member and the treatment section, the grip member including a receptacle configured to contact the treatment section and to be worn by the ultrasonic vibration of the treatment section when the grip member is closed relative to the treatment section, and an electrode section which is insulated from the receptacle and which is located apart from the treatment section when the treatment section contacts the receptacle and which is configured to function as a second electrode in the high-frequency treatment, the output device includes an ultrasonic waveform output section configured to output, to the vibration generator, a drive signal to drive the vibration generator, and a high-frequency output section configured to output a high-frequency current in the high-frequency treatment to the treatment section and the electrode section, the surgical treatment system includes a first electrical path which electrically connects the high-frequency output section and the electrode section to each other, and a second electrical path which electrically connects the high-frequency output section and the treatment section to each other, and one of the first and second electrical paths includes an electrical resistance of 10 to 1000Ω.

In the surgical treatment system according to the present referential aspect, the electrical resistance of 10 to 1000Ω is provided in one electrical path in the high-frequency treatment. The electrical resistance is less than or equal to 1000Ω. Therefore, when living tissue is gripped by the treatment section and the electrode section and thus has the high-frequency treatment carried out on it, a necessary degree of high-frequency current in the treatment is passed through the gripped living tissue, and a sufficient coagulation function can be ensured. Moreover, the electrical resistance is greater than or equal to 10Ω. This avoids sparking between the treatment section and the electrode section, and prevents sparking between the treatment section and the grip member, even when the receptacle is worn so that the treatment section and the electrode section contact each other.

In one preferred referential aspect of the present referential invention, the electrical resistance of the surgical treatment system is a noninductive resistance.

In the surgical treatment system according to the present referential aspect, the noninductive resistance is used as the electrical resistance, so that heat generation in the electrical resistance is avoided. This prevents the surgeon from feeling discomfort from a temperature rise, and eliminates the need to provide an additional cooling mechanism.

In one preferred referential aspect of the present referential invention, the noninductive resistance of the surgical treatment system is provided in the surgical treatment apparatus.

When the surgical treatment apparatus is provided with the electrical resistance in the surgical treatment system according to the present referential aspect, the surgeon tends to feel discomfort from heat generated in the electrical resistance. When an additional cooling mechanism is provided in the surgical treatment apparatus, the surgical treatment apparatus increases in size and decreases in operability. In the present referential aspect, the noninductive resistance is used as the electrical resistance provided in the surgical treatment apparatus. This avoids heat generation in the electrical resistance, and prevents the surgeon from feeling discomfort. This also eliminates the need to provide an additional cooling mechanism in the surgical treatment apparatus and prevents the surgical treatment apparatus from increasing in size and decreasing in operability.

Other characteristic technical matters of the present invention are additionally noted below.

NOTE

Additional Section 1

A surgical treatment apparatus configured to be held and operated by a surgeon comprising:

a vibration generator configured to generate ultrasonic vibration;

a vibration transmission section configured to axially transmit the ultrasonic vibration generated in the vibration generator from a proximal end portion to a distal end portion, the vibration transmission section including a treatment section which is formed at the distal end portion of the vibration transmission section, and which is configured to ultrasonically vibrate in an ultrasonic treatment and configured to function as a first electrode in a high-frequency treatment; and a grip member which is openable or closable relative to the treatment section and which is configured to be closed relative to the treatment section to grip living tissue between the grip member and the treatment section, the grip member including a receptacle configured to contact the treatment section and to be worn by the ultrasonic vibration of the treatment section when the grip member is closed relative to the treatment section, an electrode section which is insulated from the receptacle and which is located apart from the treatment section when the treatment section contacts the receptacle, and which is configured to function as a second electrode in the high-frequency treatment, and a regulating section which is insulated from the electrode section, the regulating section being configured to contact the treatment section before the electrode section to regulate contact between the electrode section and the treatment section when the grip member is closed relative to the treatment section after the receptacle is worn more than a predetermined amount.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A surgical treatment apparatus configured to be held and operated by a surgeon, the surgical treatment apparatus comprising:

a vibration generator configured to generate ultrasonic vibration;

a vibration transmission section configured to axially transmit the ultrasonic vibration generated in the vibration generator from a proximal end portion to a distal end portion;

a treatment section which is formed at the distal end portion of the vibration transmission section, and which is configured to ultrasonically vibrate in an ultrasonic treatment and configured to function as a first electrode in a high-frequency treatment;

a grip member which is provided to be openable or closable relative to the treatment section, and which is configured to be closed relative to the treatment section to grip living tissue;

an electrode section which is provided in the grip member, and which is configured to function as a second electrode in the high-frequency treatment;

a receptacle which is provided in the grip member and made of an insulating material, and which is configured to abut onto the treatment section so that a clearance is formed between the electrode section and the treatment section when the grip member is closed relative to the treatment section, the receptacle being configured to be worn away by the ultrasonic vibration of the treatment section when the grip member is closed relative to the treatment section; and a regulating section which is provided in the grip member and insulated from the electrode section, and which is made of a material harder than the receptacle, a closing-direction side end of the regulating section, not protruding from the receptacle toward a closing direction, the regulating section being to be exposed from the receptacle in the closing direction when the receptacle is worn away more than a predetermined amount, and the regulating section being configured to contact the treatment section before the electrode section to regulate contact between the electrode section and the treatment section, when the grip member is closed relative to the treatment section, in a state that the regulating section is exposed from the receptacle.

2. The surgical treatment apparatus according to claim 1, wherein the treatment section includes an abutting portion onto which the receptacle abuts when the grip member is closed relative to the treatment section, a first electrode surfaces formed on a first width direction side of the abutting portion if the first width direction is one of directions which are perpendicular to axial directions of the vibration transmission section and perpendicular to opening-and-closing directions of the grip member relative to the treatment section, and a second electrode surface formed on a second width direction side of the abutting portion if the second width direction is a direction opposite to the first width direction, and the electrode section includes a first electrode receiving surface which is disposed to face the first electrode surfaces when the grip member is closed relative to the treatment section, and in which a distance from the first electrode surface is increased as it goes toward the first width direction, a second electrode receiving surface which is disposed to face the second electrode surface when the grip member is closed relative to the treatment section, and in which a distance from the second electrode surface is increased as it goes toward the second width direction.

3. The surgical treatment apparatus according to claim 1, wherein the regulating section has strength to be able to cause cracks in the vibration transmission section when the regulating section contacts the treatment section.

4. The surgical treatment apparatus according to claim 3, wherein the treatment section includes a stress concentration region on which stress concentrates when the treatment section is ultrasonically vibrated, and the regulating section is configured to contact the stress concentration region.

5. A surgical treatment system comprising:

the surgical treatment apparatus according to claim 3;

an output device configured to perform an output to the surgical treatment apparatus; and a connector which electrically connects the surgical treatment apparatus and the output device to each other, wherein the output device includes an ultrasonic waveform output section configured to output, to the vibration generator, a drive signal to drive the vibration generator, a high-frequency output section configured to output a high-frequency current used in the high-frequency treatment to the treatment section and the electrode section, a crack detection section configured to detect whether the treatment section has cracked, and a control section configured to control the ultrasonic waveform output section and the high-frequency output section, the control section being configured to stop the output of the drive signal to the vibration generator by the ultrasonic waveform output section and also to stop the output of the high-frequency current to the treatment section and the electrode section by the high-frequency output section when the crack detection section detects cracks.

* * * * *

UNITED STATES PATENT AND TRADEMARK OFFICE
CERTIFICATE OF CORRECTION

PATENT NO. : 8,663,223 B2  
APPLICATION NO. : 13/281875  
DATED : March 4, 2014  
INVENTOR(S) : Shinya Masuda et al.

Page 1 of 1

It is certified that error appears in the above-identified patent and that said Letters Patent is hereby corrected as shown below:

Title page, item (73) Assignee should read as follows: Olympus Medical Systems Corp. (JP)

Signed and Sealed this  
Twelfth Day of August, 2014

Michelle K. Lee  
*Deputy Director of the United States Patent and Trademark Office*